(12) United States Patent
Mizutani

(10) Patent No.: US 7,074,214 B2
(45) Date of Patent: Jul. 11, 2006

(54) INTERLABIAL PRODUCT HAVING FORM FOR FINGER SECUREMENT, AND INDIVIDUAL PACKAGE

(75) Inventor: Satoshi Mizutani, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 10/705,779

(22) Filed: Nov. 10, 2003

(65) Prior Publication Data

US 2004/0167491 A1 Aug. 26, 2004

Related U.S. Application Data

(63) Continuation of application No. PCT/JP02/04899, filed on May 21, 2002.

(30) Foreign Application Priority Data

May 22, 2001 (JP) ............................. 2001-152403
Dec. 25, 2001 (JP) ............................. 2001-391647

(51) Int. Cl.
*A61F 13/15* (2006.01)
*A61F 13/20* (2006.01)

(52) U.S. Cl. ........................ 604/385.17; 604/385.01; 604/11; 604/14; 604/904

(58) Field of Classification Search .......... 604/385.01, 604/385.17, 385.18, 904, 11–18; D24/141
See application file for complete search history.

(56) References Cited

U.S. PATENT DOCUMENTS

| 3,905,372 A | | 9/1975 | Denkinger | |
| 4,595,392 A | * | 6/1986 | Johnson et al. | 604/385.17 |
| 5,336,208 A | * | 8/1994 | Rosenbluth et al. | 604/329 |
| 5,672,165 A | * | 9/1997 | Belecky et al. | 604/383 |
| 5,695,484 A | | 12/1997 | Cox | |
| 6,131,736 A | * | 10/2000 | Farris et al. | 206/440 |
| 6,183,587 B1 | * | 2/2001 | McFall et al. | 156/201 |

FOREIGN PATENT DOCUMENTS

| JP | 50-014293 A1 | 2/1975 |
| JP | 3049907 A1 | 4/1998 |
| TW | 2819 A1 | 3/1955 |
| TW | 247431 A1 | 5/1995 |
| TW | 294591 A1 | 1/1997 |
| TW | 338315 A1 | 8/1998 |
| TW | 386030 A1 | 4/2000 |

(Continued)

OTHER PUBLICATIONS

Mizutani, et al., "Interlabial Pad", U.S. Appl. No. 10/705,406, filed Nov. 10, 2003.

(Continued)

*Primary Examiner*—Jacqueline F. Stephens
(74) *Attorney, Agent, or Firm*—Darby & Darby

(57) ABSTRACT

The present invention relates to an interlabial product and an individual wrapping body provided with a form for securing a finger, and a manufacturing method therefor, and provides an interlabial pad individual wrapping container which can be used as a suitable operation member when fixing or unfixing the interlabial pad.

Two left hand fingers are inserted in the finger insertion openings (13A, 13B) formed by the belt body (12) attached to the wrapping container (1), to separate the wrapping container (1) into the sections (1A) and (1B) along the separation part (15) by opening these fingers to the left and right, and in this state as it is, the insertion work is carried out for fixing the interlabial pad (2) held on a right hand fingertip between labia.

15 Claims, 8 Drawing Sheets

FOREIGN PATENT DOCUMENTS

| | | |
|---|---|---|
| TW | 386872 A1 | 4/2000 |
| TW | 394681 A1 | 6/2000 |
| TW | 416847 A1 | 1/2001 |
| TW | 442278 A1 | 6/2001 |
| TW | 450802 A1 | 8/2001 |
| TW | 454503 A1 | 9/2001 |
| TW | 470640 A1 | 1/2002 |
| TW | 524677 A1 | 3/2003 |
| WO | WO-98/08475 A1 | 3/1998 |
| WO | WO-99/01093 A1 | 1/1999 |
| WO | WO-99/01096 A1 | 1/1999 |
| WO | WO-99/26575 A1 | 6/1999 |
| WO | WO-00/40197 A1 | 7/2000 |

OTHER PUBLICATIONS

Mizutani, et al., "Interlabial Pad", U.S. Appl. No. 10/705,408, filed Nov. 10, 2003.
Mizutani, et al., "Interlabial Pad", U.S. Appl. No. 10/705,780, filed Nov. 10, 2003.
Mizutani, et al., "Interlabial Pad and Package Thereof", U.S. Appl. No. 10/705,404, filed Nov. 10, 2003.
Mizutani, et al, "Interlabial Pad and Package", U.S. Appl. No. 10/706,303, filed Nov. 10, 2003.
Mizutani, et al., "Interlabial Pad", U.S. Appl. No. 10/705,407, filed Nov. 10, 2003.
Mizutani, et al., "Interlabial Pad", U.S. Appl. No. 10/705,403, filed Nov. 10, 2003.
Mizutani, et al., "Individual Packaging Body and Outer Vessel Therefor", U.S. Appl. No. 10/705,402, filed Nov. 10, 2003.
Mizutani, et al., "Interlabial Pad Individual Packaging Vessel, and Individual Packaging Body", U.S. Appl. No. 10/705,781, filed Nov. 10, 2003.
Mizutani, et al., "Interlabial Pad", U.S. Appl. No. 10/705,812, filed Nov. 10, 2003.
Mizutani, et al., "Interlabial Pad", U.S. Appl. No. 10/705,811, filed Nov. 10, 2003.
Mizutani, et al., "Interlabial Pad Individual Packaging Body", U.S. Appl. No. 10/705,669, filed Nov. 10, 2003.
Mizutani, et al., "Interlabial Pad", U.S. Appl. No. 10/705,778, filed Nov. 10, 2003.
Mizutani, et al., "Interlabial Pad Individual Packaging Vessel", U.S. Appl. No. 10/705,673, filed Nov. 10, 2003.
Mizutani, et al., "Flap-Equipped Interlabial Pad", U.S. Appl. No. 10/705,670, filed Nov. 10, 2003.
Mizutani, et al., "Interlabial Pad", U.S. Appl. No. 10/705,399, filed Nov. 10, 2003.
Supplementary European Search Report for EP 02 77 1759 Completed on Nov. 30, 2004.

* cited by examiner

INTERLABIAL PRODUCT HAVING FORM FOR FINGER SECUREMENT, AND INDIVIDUAL PACKAGE

CROSS-REFERENCE TO RELATED APPLICATIONS

This application is a Continuation of International Application No. PCT/JP02/04899 filed May 21, 2002, which application published in Japanese on Nov. 28, 2002 as WO 02/094163 A1 under PCT Article 21(2).

BACKGROUND OF THE INVENTION

1. Technical Field

The present invention relates to an interlabial product and an individual wrapping body provided with a form for ensuring finger insertion, and a manufacturing method thereof.

2. Background Art

Conventionally, a sanitary napkin and a tampon are used generally as a female sanitary product. Here, there have been great efforts to prevent the leak of menstrual blood from a gap caused by poor adhesion near the ostium vaginae as for the sanitary napkin. Moreover, as for the tampon, there have been great efforts for relieving a foreign feeling and discomfort when the sanitary product is put on and for lowering the difficulty in insertion of the product due to the nature of the product.

Under such situation, an interlabial product has attracted people as a sanitary product positioned between the sanitary napkin and the tampon in recent years.

The interlabial product is fixed by inserting it between the labia, having characteristics that it is difficult to cause the leak of menstrual blood because of higher adhesion to the body than that of the sanitary napkin and psychological resistance thereof on wearing is lower than that of the tampon which is inserted into the vagina. Moreover, it is sanitary and clean because the range of the body or the skin soiled with menstrual blood is small as compared with the sanitary napkin which is used by attaching to an underwear. Further, since the product size of the interlabial product is smaller than that of the sanitary napkin, a feeling of wearing is not deteriorated generally and it is comfortable.

However, compared with the sanitary napkin, the interlabial product has the disadvantage that it is more difficult to insert than the napkin, because the interlabial product is to be inserted between the labia which are difficult to be seen. Moreover, when it is not inserted in a proper position, leakage may cause serious damage because the interlabial product is smaller than the napkin in size. Also, compared with the tampon, it may be more possible for the product to be mis-inserted than for the tampon.

As a product improved in the difficulty of insertion of such an interlabial pad, PCT International Patent Publication No. WO99/56689 discloses a pad having a structure provided with a projecting part on the back of the contact side with a body. According to this structure, a wearer can insert the pad by picking up said projecting part, therefore, the insertion is regarded easier in this case than in the case without said projecting part.

However, in such a structure, the insertion point is detected by a fingertip of the wearer, therefore, the wearer has to insert the pad by intuition, and it is quite difficult for the wearer to locate the right insertion point. Namely, a conventional interlabial product has not been developed well enough to be inserted with a wearer's confidence for the right insertion point. Especially, and since a woman often keeps her nails long or often wears fake nails, it is sometimes almost impossible for her to insert the above-mentioned conventional interlabial product in the right place. Moreover, it is also difficult to put the interlabial pad on the pudenda utilizing only the projecting portion to be pinched so as to make a close contact between them.

Thus, the conventional interlabial product mentioned above have not been developed enough to facilitate the insertion by properly locating the insertion point and reduce the occasion at mis-insertion or allow the product to have a sufficiently close contact with the pudenda. Further, such a situation sometimes occur, as menstrual blood etc. adhere to a fingertip at the time of inserting the pad, which may cause the wearer to form a sense of resistance when the interlabial product is used.

DISCLOSURE OF THE INVENTION

The present invention has been made considering the above-described task, and the purpose is to provide an interlabial product of a structure which facilitates exact and sanitary insertion of the product between labia of a woman, and to provide an individual wrapping body enclosing such product.

In order to achieve the above-described task, the inventors have developed an interlabial product provided with a structure permitting to insert it so that it sufficiently and closely adheres to vagina while a wearer is confirming an insertion position by utilizing a sensitive finger cushion. To be more concrete, the product is characterized in that the interlabial product is curled up to form a pocket allowing a fingertip to be smoothly inserted so that the product can smoothly be inserted between the labia by the finger inserted in the pocket.

To be more concrete, the present invention provides as follows.

(1) An interlabial product which comprises a water-permeable surface side sheet, a back side sheet, and an absorbent body for absorbing body fluid disposed between the surface side sheet and the back side sheet, the product comprising a cylindrical portion in which a finger can be inserted when it is used; and wherein said cylindrical portion comprises said surface side sheet, said back side sheet, and said absorbent body.

The cylindrical portion may be formed only when a finger is inserted therein, and does not need to be cylindrical before finger insertion. For example, the cylindrical portion includes a portion to form a cylindrical structure at the time of insertion of a finger therein even though the cylindrical portion is collapsed and folded up in two when it is enclosed in an individual wrapping body.

A wearer can secure the interlabial product by inserting a finger into the cylindrical portion so that a finger cushion of the finger is faced to an inner face of the cylindrical portion. The wearer can thereby securely holds the interlabial product, until the interlabial product is inserted between the labia. Following this, by making the length direction of the interlabial product aligned in the same direction of the finger insertion, the vulvar slit and the interlabial product are aligned in the same direction so that it is easier for the wearer to insert the product in the labia.

Further, since the wearer can insert the interlabial product while detecting the insertion point with a ball of the finger and while the finger pressure for pushing the interlabial product between the labia can uniformly be applied in the longitudinal direction, even closer contact between the interlabial and the inside of the labia may be made.

(2) The interlabial product according to (1), comprising a flap portion as a sector form area adjacent to said cylindrical portion, wherein said flap portion comprises said surface side sheet, said back side sheet, and said absorbent body.

Since the finger can be inserted into the cylindrical portion from a flap portion, the insertion can easily be performed.

(3) The interlabial product according to (1) or (2), characterized in that said cylindrical portion gets gradually smaller in diameter along a finger insertion direction when it is used.

While the finger is being inserted, the deeper the finger is inserted in the cylindrical portion, the more difficult the finger insertion becomes so that the interlabial product can naturally be fixed on the finger. Therefore, the shape of the cylindrical portion in accordance with the present invention includes not only a simple cylindrical shape but also a plummet shape, for example, a conic shape, a pyramid shape, a truncated cone shape, a truncated pyramid shape, etc.

(4) The interlabial product according to any one of (1) to (3), characterized in that said cylindrical portion is extended up to an end portion of the interlabial product along the finger insertion direction, and that said cylindrical portion covers a wearer's finger inserted in said cylindrical portion.

A wearer can perform a sanitary inserting operation without touching the labia or menstrual blood adhering to the labia at the time of insertion of the interlabial product between the labia.

(5) The interlabial product according to any one of (1) to (4), characterized in that said cylindrical portion is extensible or elastic at least in a lateral direction.

The interlabial product changes its shape in accordance with the inserted finger so as to be secured by the finger. Moreover the wearer can identify the wear point more easily.

(6) The interlabial product according to any one of (1) to (5), characterized in that the flap comprises a pair of flap pieces.

A wearer may visually check a finger insertion opening of the cylindrical portion through between a pair of flap pieces, as well as visually recognize the depth of the cylindrical portion so that even an inexperienced wearer can easily perform the wearing operation.

(7) The interlabial product according to any one of (1) to (6), characterized in that a tacking agent is applied on an inner surface of said cylindrical portion for a fingertip of the finger.

The interlabial product is secured and is inserted in the labia without a positional deviation between the finger and the product.

(8) The interlabial product according to any one of (1) to (7), wherein said absorbent body is enclosed between said surface side sheet and said back side sheet, and wherein said back side sheet is disposed inside of said cylindrical body.

The interlabial product may be what is called a laminated type.

(9) The interlabial product according to any one of (1) to (7), wherein said absorbent body and said back side sheet are enclosed in said surface side sheet, and wherein said surface side sheet is disposed inside and outside of said cylindrical body.

The interlabial product may be what is called an enclosed type.

(10) The interlabial product according to any one of (1) to (9), wherein said interlabial product is a product for incontinence.

According to the interlabial product according to the present invention, the product can be used for incontinence absorb product. Since the ostium vaginae where the menstrual blood is discharged and the urethral meatus where urine is discharged locate between labia, and the interlabial product according to the present invention to be used between labia can also absorb urine.

As described hereinbefore, the product according to the present invention can absorb urine between the labia, especially around the urethral meatus and is useful for the absorbing product for incontinence, especially for a light incontinence.

(11) The interlabial product according to any one of (1) to (9), wherein said interlabial product is a product for absorbing vaginal discharge.

In accordance with the present invention, the interlabial product can be used for the product for absorbing the vaginal discharge. Since the interlabial product is used between the labia, it can absorb the excretion other than the menstrual blood from the ostium vaginae for the use therefore (for absorbing the vaginal discharge).

As described above, the product can absorb the vaginal discharge in order to reduce the discomfort to the wearer, and is useful for the wearer who is not menstruating.

(12) An individual wrapping body comprising the interlabial product recited in any one of (1) to (11), and a wrapping sheet for entirely covering and enclosing said interlabial product.

Since the interlabial product is compactly enclosed in a wrapping sheet in a sanitary condition before use, a single interlabial product can be taken out of an individual wrapping body as required. A releasable folded part, a tab, perforations, or a small cut for opening may be formed on the individual wrapping body.

(13) The individual wrapping body according to (12), wherein said interlabial product is folded up and enclosed so that the flap pieces open when the individual wrapping body is unwrapped.

Since the product is folded when it is enclosed, it is compactly packaged. Preferably, the product is folded in two in the lateral direction along the longitudinal center line. And, since the flap pieces can be opened when the individual wrapping body is unwrapped, the finger can easily be inserted into the cylindrical portion.

(14) The individual wrapping body according to (12) or (13), characterized in that the interlabial product is disposed so that the finger insertion opening of said cylindrical portion is positioned to face the unwrapping opening of said individual wrapping body.

Since the finger is positioned along the longitudinal direction on the garment face side of the interlabial product, the inserting operation is speedily operated and a close contact with the labia is secured more by applying the finger pressure over the longitudinal direction of the interlabial product for inserting the product between the labia.

Moreover, since the direction for securing the interlabial product by the finger to the longitudinal direction of the garment face side of the interlabial product is specified, as well as the finger cushion is made to face the body side when the interlabial product is secured by the finger, the interlabial product can be inserted while the wearer is locating the insertion point by the sensitive finger cushion even if the insertion between the labia is difficult to be checked visually. Also, since a direct contact between the labia and the finger can be prevented when the interlabial product is inserted in the labia, the inserting operation can be performed in a sanitary condition.

(15) A method for manufacturing an individual wrapping body comprising: a process for folding the interlabial product recited in any one of (1) to (11) in two parts in a lateral direction along a longitudinal center line; and a process for enclosing said interlabial product in the wrapping sheet.

The individual wrapping sheet can easily be manufactured. Any enclosing mode in the wrapping sheet may apply. Preferably, the interlabial product is formed to be symmetrical to the longitudinal center line.

BEST MODE FOR CARRYING OUT THE INVENTION

[Constitution]

Figure 1:
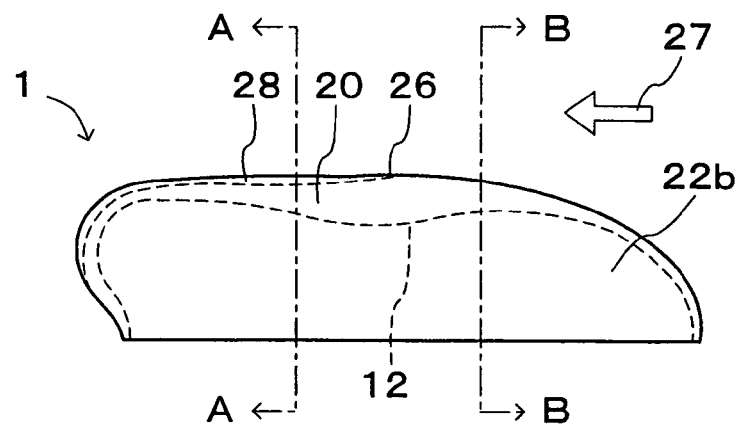
FIG. 1 is a top view showing an interlabial product in accordance with one embodiment of the present invention.
Figure 2:
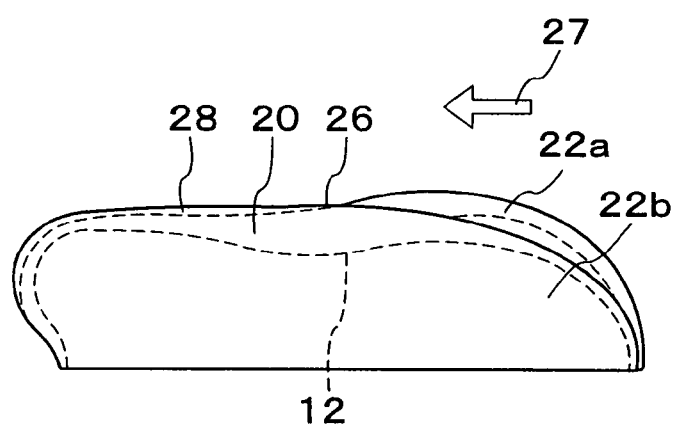
FIG. 2 is a schematic perspective view showing the interlabial product in accordance with one embodiment of the present invention.
Figure 3:
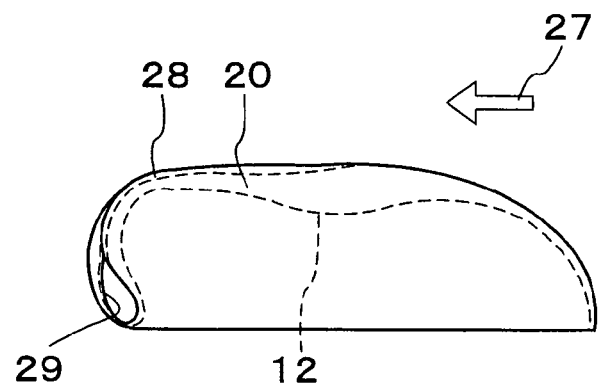
FIG. 3 is a schematic perspective view showing the interlabial product in accordance with one embodiment of the present invention.
Figure 4:
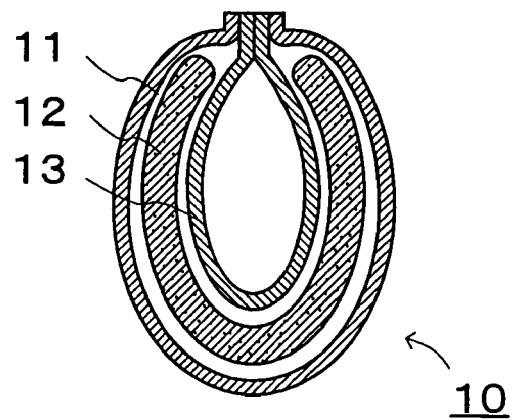
FIG. 4 is a schematic cross-sectional view taken along the arrowed line A—A of FIG. 1.
Figure 5:
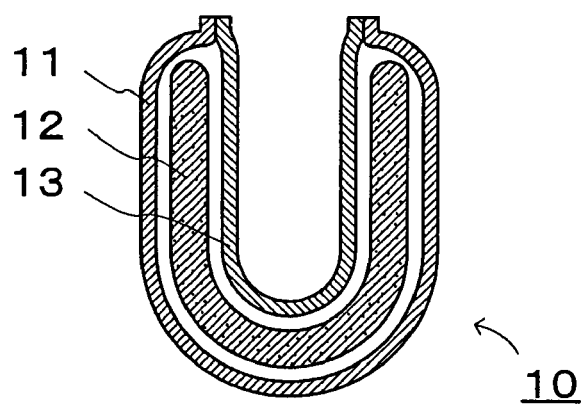
FIG. 5 is a schematic cross-sectional view taken along the arrowed line B—B of FIG. 1.

FIG. 1 is a schematic plan view showing the interlabial product in accordance with one embodiment of the present invention. FIG. 2 and FIG. 3 are schematic perspective view of the interlabial product in accordance with one embodiment of the present invention. FIG. 4 is a schematic cross-sectional view taken along the arrowed line A—A of FIG. 1. FIG. 5 is a schematic cross-sectional view taken along the arrowed line B—B of FIG. 1. FIG. 4 and FIG. 5 illustrate what is called a laminated type of the embodiment.

As shown in FIG. 4 and FIG. 5, the interlabial product 1 in accordance with this embodiment comprises a surface side sheet 11 composed of a body fluid permeable material, a back side sheet 13, and an absorbent body 12 for absorbing body fluid. The surface side sheet 11 and the back side sheet 13 are bonded together on the peripheral portion so as to enclose the absorbent body 12 and to be formed in one body. The surface side sheet 11 and the back side sheet 13 are bonded by means of heat emboss processing and/or bonding with a hot-melt type adhesive.

The interlabial product is provided with a cylindrical portion 20 permitting to insert a finger therein when it is used, and a flap portion as a fan-top area composed of a pair of flap pieces 22a, 22b arranged adjacent to said cylindrical portion in the opposite direction of finger insertion direction 27. The cylindrical portion is comprised of the surface side sheet 11, the absorbent body 12, and the back side sheet 13. The pair of the flap pieces 22a, 22b are also, as the cylindrical portion 20, comprised of the surface side sheet 11, the absorbent body 12, and the back side sheet 13. The surface side sheet 11, the absorbent body 12, and the back side sheet 13 are continuous with the flap pieces 22a, 22b via the cylindrical portion 20.

The cylindrical portion 20 is bonded from the side edge portion 28 up to the corner portion along the longitudinal direction of the back side sheet 13, while the flaps 22a, 22b are not bonded along the longitudinal side edge faces of the back side sheet 13. When these are bonded, the back side sheet 13 is placed inside of the cylindrical portion.

The side edge portions to be bonded together need at least 10% or longer of the length in the longitudinal direction of the interlabial product, and more preferably, they have 30–60% of the length.

In this embodiment, as shown in FIG. 3, a part of fingertip portion is not bonded so as to form an opening 29. The bonded portion may be arranged in such a structure as the bonded portion starts with about the middle of the side edge portion of the interlabial product and extends to the end portion of the interlabial product where the fingertip end portion is located. Here, to extend to the end portion of the interlabial product where the fingertip end portion is located means that a wearer's finger can be well covered with the cylindrical portion up to the fingertip. When the wearer's finger is well covered with the cylindrical portion up to the fingertip, the opening 29 either may be formed or may not be formed.

Compared with the cylindrical portion 20, the flap pieces 22a, 22b are open in the lateral direction. In such a manner, the finger insertion opening 26 of the cylindrical portion as well as the depth of the cylindrical portion become visible to a wearer, therefore, even an inexperienced wearer can naturally be directed to the operation for securing the interlabial product by her finger.

The cylindrical portion may gradually become smaller in diameter along the direction 27 of finger insertion when it is used. For example, the side edge portion of the interlabial product can be provided with this structure by widely arranging the width of the side edge portion in the neighborhood of the finger insertion opening 26, and gradually narrowing it in the direction 27 of finger insertion of the cylindrical portion 20.

The side edge portion of the interlabial product can also be provided with this structure by another method in which the absorbent body 12 positioned in the neighborhood of the finger insertion opening 26 is narrowly arranged in width and the absorbent body 12 is gradually increased in width in the direction 27 of the finger insertion of the cylindrical portion 20. Otherwise, both methods may be used together.

With such structure, it becomes possible to eliminate a positional deviation between the finger and the interlabial product until the product is inserted after the interlabial product is secured by inserting the finger into the cylindrical portion thereof, and this allows the interlabial product to obtain even contact surfaces on the right and the left inner walls of labia.

Inside of the individual wrapping body, a type of the interlabial product laminated approximately along the longitudinal center line is folded up in the lateral direction so that the back side sheet is faced to each other. Therefore, the cylindrical portion 20 is not cylindrical either inside of the individual wrapping body, but is folded flat in two. For example, in the case of the laminated type, it is formed by being folded in such a way as the garment side of the back side sheet is faced together approximately along the longitudinal center line, and the mutually overlapping parts of the right and left side edge portions are bonded together.

In one embodiment of the present invention, as shown in FIG. 4 and FIG. 5, the interlabial product may be what is called such a laminated type as the side edges are formed by bonding the surface side sheet and the back side sheet together on the side edge portions of the absorbent body to prevent the absorbent body from coming off.

[Enclosed Type]

Figure 6:
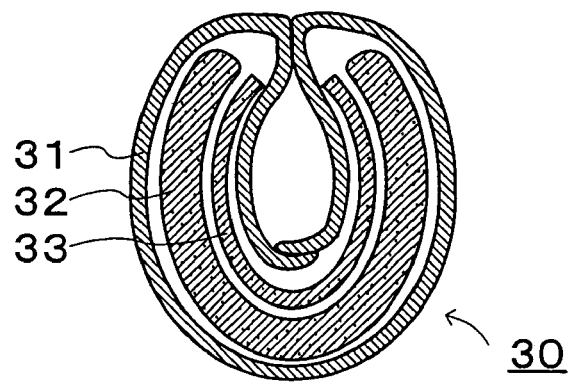
FIG. 6 is a schematic cross-sectional view of an interlabial product in accordance with another embodiment of the present invention.
Figure 7:
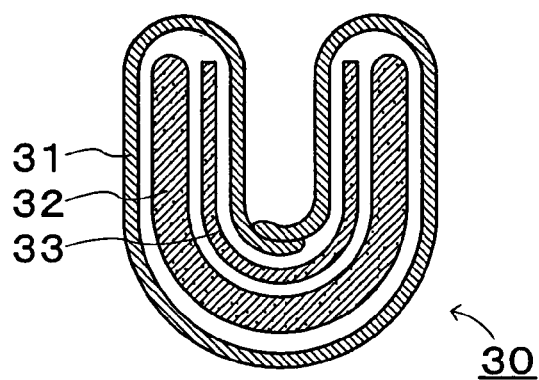
FIG. 7 is a schematic cross-sectional view of an interlabial product in accordance with another embodiment of the present invention.

In the interlabial product in accordance with another embodiment of the present invention, as shown in FIG. 6 and FIG. 7, the interlabial product may be what is called an enclosed type in which the back side sheet 33 is arranged on the garment surface side of the absorbent body 32, and then the surface side sheet 31 encloses the absorbent body 32 and the back side sheet 33. According to this embodiment, the interlabial product comprises the water-permeable surface side sheet 31, the back side sheet 33, and the absorbent body 32 for absorbing body fluid arranged between the surface side sheet 31 and the back side sheet 33. Namely, in FIG. 6 and FIG. 7, the surface side sheet 31, the absorbent body 32, the back side sheet 33, and the surface side sheet 31 are arranged in the order from the outside toward the inside of the cylindrical portion of the interlabial product. The surface side sheet 31 is continuous. In the case of an enclosed type, to form the cylindrical portion, the back side sheet 33 and the absorbent body 32 are mutually bonded with the back side sheet inside and the absorbent body 32 outside from a part of the longitudinal side edge portion of the surface side sheet 31 to corner portion.

According to the embodiment shown in FIG. 6 and FIG. 7, the surface side sheet 31 is overlapped and bonded together in the neighborhood of the inside longitudinal center line. However, the overlapping position is not limited to this position.

Also in the case of the enclosed type, a cylindrical portion permitting to insert a finger therein when it is used, and flap portions as sectorial top areas in the direction opposite to the finger insertion direction adjacent to said cylindrical portion are formed on the interlabial product. Namely, also in the case of the enclosed type, the appearance is as shown in FIG. 1–FIG. 3. The cylindrical portion is comprised of, the surface side sheet 31, the absorbent body 32, the back side sheet 33, and the surface side sheet 31 in the order from the outside to the inside, and just like the cylindrical portion, the flap pieces 22a, 22b are also comprised of the surface side sheet 31, the absorbent body 32, the back side sheet 33, and the surface side sheet 31. The surface side sheet 31, the absorbent body 32, and back side sheet 33 are continuous from the cylindrical portion to the flap portions.

The embodiment of the laminated type is mainly explained in the following, however, the present invention is not to be restricted to the embodiment of this type.

[Tensibility]

The finger insertion portion, namely, the cylindrical portion may be arranged so as to flexibly correspond to various sizes of wearers' fingers by being provided with elasticity or tensibility at least in the lateral direction in the neighborhood of the side edge portion. Such characteristics can be obtained from corrugation processing in which the side edge portion is formed to be gathered by pressing the side edge portion with a male and a female molds having recessed and projecting portion arranged with intervals in the longitudinal direction. Otherwise, an elastic material, for example, rubber may be used for the side edge portion. A fiber sheet having elasticity, especially, a fiber sheet containing elastic fiber, for example, non-woven fabric containing urethane fiber is also applicable.

[Breaking Strength]

The finger insertion portion, namely, the cylindrical portion, in which a wearer can insert a finger in the longitudinal direction of the interlabial product, is formed on the garment surface side of the back side sheet by bonding together the right and left side edge portions of the interlabial product folded along the longitudinal centerline.

In the bonding portion for bonding the side edge portions, the breaking strength is preferred to be at least 30 cN or higher. The breaking strength is a value measured when the interlabial product is cut apart in the longitudinal direction along the folded part and the cut portions are held with chucks, respectively, and the maximum tensile strength is measured by stretching the bonded portion at a speed of 100 mm/min. More preferably, the breaking strength is in a range of 40–300 cN, and it is most preferable that the breaking strength ranges 40–150 cN.

[Tacking Agent]

Figure 8:
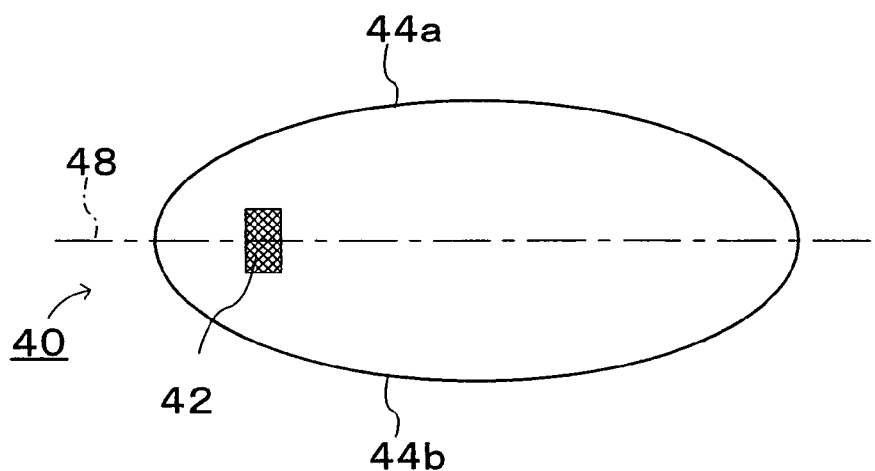
FIG. 8 is a schematic perspective view of an interlabial product in accordance with another embodiment of the present invention.

As shown in FIG. 8, a tacking agent 42 may be applied to the inner surface of the cylindrical portion of the interlabial product. FIG. 8 is a development before the cylindrical portion is formed, and the peripheral portion 44a and the peripheral portion 44b are bonded together to form the cylindrical portion. After the cylindrical portion has been formed, the tacking agent is applied to the inner surface 42 of the cylindrical portion. As to a preferred arrangement of the tacking agent, it is preferred that the tacking agent is applied on the ball of the fingertip and along the longitudinal direction of the folded part 48 of the interlabial product.

When the tacking agent is arranged near the side of the ball of the fingertip, a press force is applied to the interlabial product by the fingertip when the interlabial product is inserted in the labia, therefore, the press force can prevent the finger from deviating. When the finger is drawn out of the cylindrical portion after insertion, the finger can be drawn out by relaxing the pressint force at the fingertip, and releasing the finger in the direction of the crotch from the inner surface of the cylindrical portion. In this case, the tacking agent is applied nearer to the folded portion than to the bonding portion for bonding the side edge portions of the interlabial product.

The interlabial product before use is folded along the folding portion, and the back side sheet may be tacked together via the tacking agent. In this case, tacked portions of the back side sheet via the tacking agent may be separated by the wearer's finger insertion by a wearer into the finger insertion portion (cylindrical portion), and the tacking agent is exposed to the inner surface of the cylindrical portion, to come into contact with the inserted finger.

The tacking agent is applied in a form of lines, a sprayed form, a meshed form, an Ω-letter-form, a form of dots, etc. Moreover, a preferred tacking agent is provided with a sufficient anchor effect so as not to be left on the finger when the finger is drawn out, and the tacking agent is preferred to be applied by means of using a coater or printing.

Figure 18:
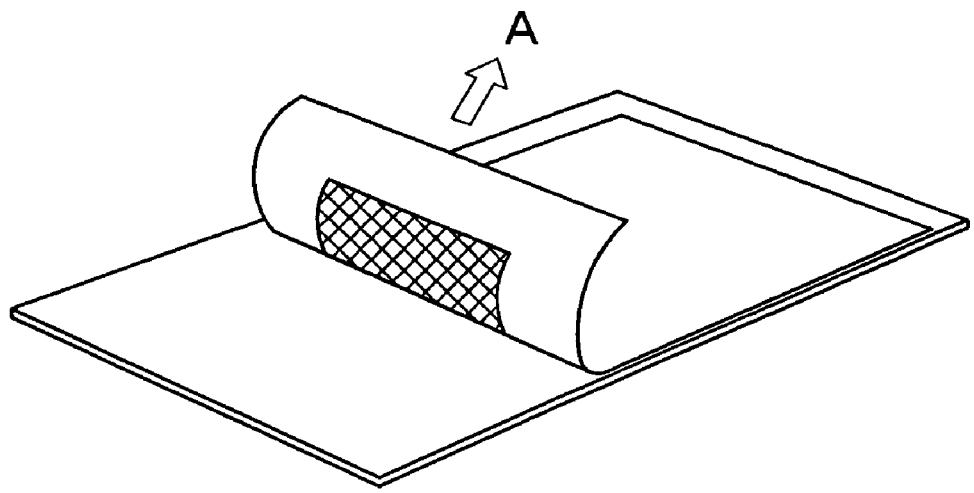
FIG. 18 is an explanatory drawing for explaining a method of measuring the peel strength of an adhesive in a method for evaluating adhesion of the adhesive to be applied on the body side surface of the surface side sheet.
Figure 19:
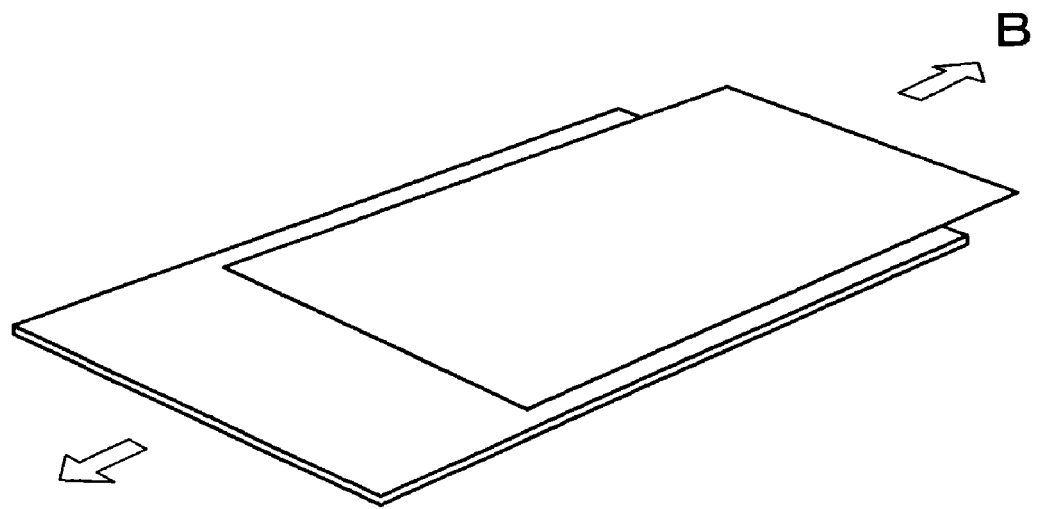
FIG. 19 is an explanatory drawing for explaining a method of measuring the shear strength of an adhesive in a method for evaluating adhesion of the adhesive to be applied on the body side surface of the surface side sheet.

An example of a method for evaluating adhesion of the tacking agent will be explained below. Such an evaluation method is through measuring peel strength (refer to FIG. 18) of an adhesive, and shear strength (refer to FIG. 19) of the adhesive, and is performed by using a constant speed stretch tensile tester and a 80 mm long and 50 mm wide stainless plate. When the evaluation test is carried out, a polyethylene film of about the same size as the stainless plate is coated with an adhesive so as to be 25 mm wide and 50 mm long, and is left at a room temperature (20 degree C.) for 30 minutes beforehand. Next, the polyethylene film is lightly superposed on the stainless plate so that the adhesive is in contact with the stainless plate, and is rolled by a 2 kg roller only one way. And then, the film is left at a room temperature (20 degree C.) for 30 minutes to make a test specimen. In the peel strength test, the polyethylene film part of the test specimen made as described above is peeled by pulling it in the direction of the arrow A as shown in FIG. 18, and in the shear strength test, the polyethylene film part is pulled in the direction of the arrow B shown in FIG. 19. However, as the test conditions, a chuck distance (grip distance) is specified as 70 mm, and a stretching speed is specified as 100 mm/min. When the measurements are carried out according to the above method, it is preferable that the measured peel strength of the specimen is 100–2000 mN/25 mm, and the measured shear strength of the specimen is 2900–15000 mN/25 mm. These are the values considering a load on wearer's skin.

Thus, by applying a finger-tacking tacking agent at least in the neighborhood of the finger-touch point in the finger insertion portion, sliding-caused deviation between the interlabial product and the finger can surely be prevented until the interlabial product has been fixed between the labia after the interlabial product is secured by the finger.

[Developed Shape]

Figure 9:
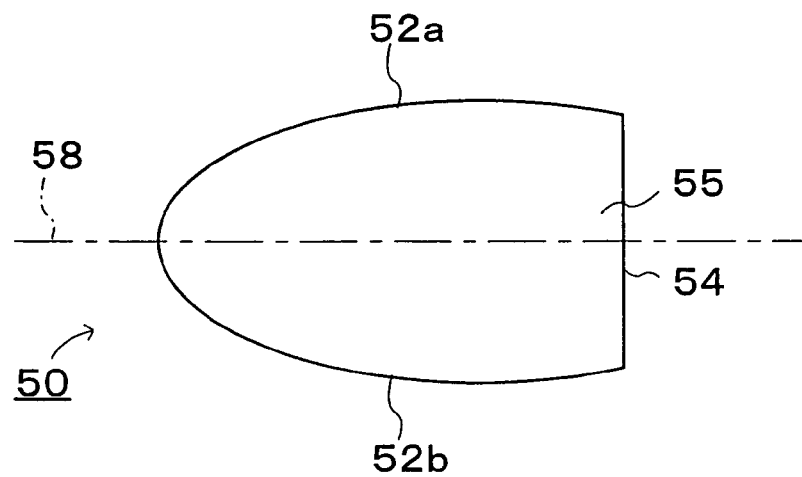
FIG. 9 is a development of the interlabial product developed on a plane in accordance with one embodiment of the present invention.
Figure 10:
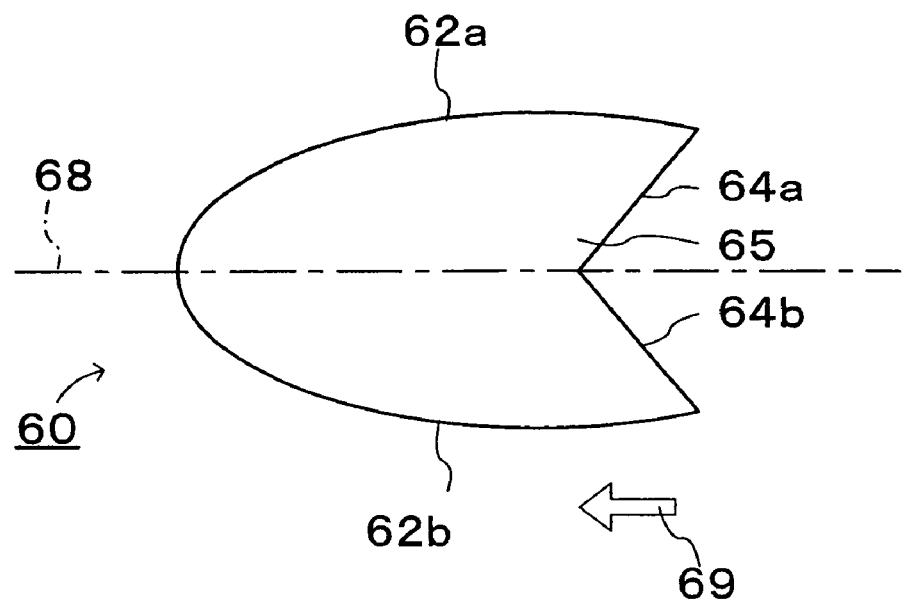
FIG. 10 is a development of the interlabial product developed on a plane in accordance with another embodiment of the present invention.

Developed shapes in accordance with one embodiment of the interlabial product when it is developed on a plane are shown in FIG. 9 and FIG. 10. The developed shape may be elliptic, egg-shaped, drop-shaped, dumbbell-shaped, or the like, however, as shown in FIG. 9 and FIG. 10, it may be an elliptic shape with a cut.

As shown in FIG. 9, as to the shape of the end portion 55 of the interlabial product 50 before the side edge portions 52a, 52b are bonded, the border line 54 connecting the side edge portions 52a, 52b of the interlabial product may be orthogonal to the longitudinal center line 58. Although the border line 54 is a straight line in FIG. 9, this may be a curved line. A preferred border line is shaped symmetrical with respect to the longitudinal center line 58.

As shown in FIG. 10, the shape of the end portion 65 of the interlabial product 60 before connecting the side edge portions 62a, 62b may be provided with the cutting lines 64a, 64b from the side edge portions 62a, 62b of the interlabial product in the direction of the finger insertion. It is preferable that the shape is formed symmetrical with respect to the longitudinal center line 68. The cutting lines are not limited to a straightline but may be a curved line.

When the interlabial product is thus formed into a shape with a cut in the end portion, an extending portion from the top of the fingertip is shortened and a form fitted to the fingertip shape can be obtained so that a wearer may recognize (from the feeling of the fingertip during insertion) that the fingertip is in the neighborhood of the top end of the interlabial product, and this makes it easier for the wearer to apply sufficient pressing force to the ostium vaginae of the menstrual blood outlet.

[Dimensions]

A lengthwise dimension (longitudinal dimension) and a widthwise dimension (lateral dimension) of the interlabial product should be determined not only within a range in which the interlabial product can be inserted and held in the labia, but also considering the adhesion to the inside of labia. The longitudinal length of the interlabial product is preferred to be 60–150 mm, more preferably, 80–120 mm. In this case, when the length is longer than 150 mm, the interlabial product has a too large contact face between the garment side surface thereof and an underwear or the like, and this causes friction force stronger than the holding strength of the interlabial product by the labia themselves, and the interlabial product is at the risk of coming off. On the other hand, when the length is shorter than 60 mm, the interlabial product cannot have a sufficient area and volume for staying between the labia, therefore, said interlabial product is prone to fall off.

The widthwise length of the interlabial product before the cylindrical portion is formed is preferred to be 10–60 mm, more preferably, 30–50 mm. In this case, if the width is wider than 60 mm, the edge portions of the interlabial product rub the femoral regions of the wearer, and this causes friction force between them every time when the wearer moves. And, if such friction holding strength exceed the force of the labia themselves holding the interlabial product, said interlabial product between the labia is in danger of falling off. Moreover, when the width is narrower than 10 mm, the interlabial product cannot have an area and a volume enough to stay between the labia, and said interlabial product is prone to fall off.

A longitudinal dimension of the absorbent body may be the same as that of the interlabial product, and may be arranged with 2–10 mm spacing considering the flexibility of the interlabial product. A width dimension of the absorbent body is arranged in a range of 30–70 mm, preferably in a range of 35–55 mm. Following this, a width dimension of the interlabial product is arranged considering ease of finger insertion in the finger insertion portion, and a dimension little influenced by body movement while being worn, and the width is arranged to be at least 40 mm or wider when the interlabial product is developed in a plane, preferably, it is arranged in a range of 50–70 mm.

A thickness of the interlabial product related to the present invention is preferred to be 0.5–20 mm, and more preferably, 2–10 mm.

Since the interlabial product is inserted between the sensitive labia, a 20 mm or thicker product gives a wearer a foreign feeling when she wears it. On the other hand, when the thickness is 0.5 mm or less, the enclosed absorbent body's volume is prone to be insufficient for absorbing menstrual blood, and the menstrual blood is in danger of oozing from the interlabial product.

The interlabial product may be used by itself, or it can be used together with a sanitary napkin by putting it on the underwear, or it can be used together with a tampon by inserting it in the vagina.

[Method for Manufacturing Laminated Type]

In the interlabial product, the surface side sheet is arranged on the body surface side of the absorbent body, and the back side sheet is arranged on the garment side of the absorbent body. Between the absorbent body and the surface side sheet or between the absorbent body and the back side sheet, a bonding agent may be applied for bonding them together.

The peripheral portion forming the periphery of the absorbent body is formed by bonding the surface side sheet and the back side sheet with each other, and the bonding is carried out by means of a sealing method such as heat-seal and ultrasonic seal, or a bonding agent such as a hot-melt type bonding agent and an emulsion-type bonding agent, or a combination of both sealing and bonding methods. Thus, the absorbing portion of the interlabial product is formed.

Following this, the absorbing layer integrating the absorbent body, the surface side sheet, and the back side sheet is folded in the lateral direction along the longitudinal center line so that the back side sheet faces itself with each other, and then, the overlapping peripheral portion is partly bonded, and is cut into a predetermined shape keeping the folded state as it is, to form the outline of the interlabial product.

[Bonding Method]

As a method for bonding the overlapping side edge portions of the interlabial product folded along the longitudinal center line, methods such as heat-seal and ultrasonic seal, or a bonding agent such as an hot-melt type bonding agent and an emulsion-type bonding agent, or the use of sealing and bonding agents together can be employed.

When the heat-seal is used, a sealing width is arranged in a range of 1–3 mm considering a favorable wear feeling. Following this, the sealing may be arranged like a continuous line, however, the arrangements such as a dashed line alternately arraying a bonded portion and a non-bonded portion, a dotted form, and a mesh form are more preferable.

A bonding agent for bonding (sticking) each material, hot-melt type bonding agent, which are generally used, can be used, and as examples, a pressure sensitive hot-melt type bonding agent and a thermo-sensible hot-melt type bonding agent can be employed. The pressure sensitive hot-melt bonding agent comprising mainly a synthetic rubber resin such as styrene-isoprene-styrene block copolymer (SIS), styrene-butadiene-styrene block copolymer (SBS), styrene-ethylene/butadiene-styrene block copolymer (SEBS), and styrene-ethylene/propylene-styrene block copolymer, and can be obtained by melt-blending therein an adhesion additive such as a terpene resin and a rosin resin and a plasticizer like wax etc.

As the thermo-sensible hot-melt bonding agents, those essentially comprising an olefin type resin having poly-α-olefin as a base resin can be employed as examples.

Thus, many kinds of bonding agents exist, however, considering stability of application, it is preferred to use a thermo-sensible hot-melt adhesive. As a thermo-sensible hot-melt adhesive having high application stability, a melt-blending of 45–55 m % poly-α-olefin, 10–15 m % plasticizer, and 35-45 m % adhesion additive can be used as an example. As to this thermo-sensible hot-melt bonding agent, 0.1–1.0 m % oxidation inhibitor and fluorescence inhibitor may be added thereto.

Such a bonding agent is applied in a line form, a spiral form, a sprayed form, an Ω-like form, etc. Moreover, since the interlabial product is inserted between the labia of a woman and is therefore formed of curved surfaces in order to create generally a soft atmosphere about the product, a printing method is suitable when an application method along the curved surfaces is selected.

When washability is considered, the bonding agent is selected from polymers in which hydroxide polymers such as polyoxyethylene-polyoxy-propyrene glycol, etc. are polymerized to thermo-plastic polyvinyl alcohol resin, starch paste, gelatin, polyester polyol resin, or mixtures of a pressure sensitive adhesive essentially comprising a synthetic rubber such as styrene-ethylene/butadiene-styrene block copolymer (SEBS), styrene-isoprene-styrene block copolymer (SIS), styrene-butadiene-styrene block copolymer (SBS), etc., and water-soluble materials such as hydrophilic activator, starch paste, gelatin, etc.

[Materials for Surface Side Sheet]

The surface side sheet is preferred to be water-permeable and to be selected from materials not stimulative to skin. For example, non-woven fabric obtained from the manufacturing methods of melt-blown, spunbond, through-air, point-bond, needle-punch, spun lace, etc. can be used, however, considering a ratio of contact with the inner wall of labia, it is preferable to singly use non-woven fabric obtained from the manufacturing methods of spun lace, melt-blown, needle-punch, etc. or to use some of them combined.

It is also preferable to use single or mixed sheet-like fiber selected from rayon, acetate, cotton and pulp as natural fiber, or homo-fiber made of a synthetic resin or conjugated fiber of a sheath-core structure, hydrophilization-treated synthetic resin, etc. Concretely, spun lace non-woven fabric etc. can be used, which is obtained by adjusting mixed fiber in proportion of 10–1 m % synthetic fiber, 4–30 m % natural cotton, 60–95 m % rayon or acetate to with a specific weight per unit area 20–50 g/m$^2$, confounding the fiber itself by means of the water confounding method, drying it, and adjusting the thickness to 0.1–1.0 mm.

The reason for mixing the synthetic resin in the above spun lace non-woven fabric is that the volume and inter-fiber distance can easily be maintained even when the surface side sheet gets wet from contact with menstrual blood. Further, the reason for a little low compounding ratio of the synthetic fiber is that the fiber rigidity is maintained even when the fiber gets wet with menstrual blood, therefore, compounding more than necessary is in danger of hurting the inner wall of labia due to the fiber rigidity. Preferred synthetic fiber is single fiber such as polypropylene, (PP), polyethylene (PE), and polyethylene terephthalate (PET), or fiber formed from graft polymerization of PE and PP, further, a sheath-core structure of which the core is PP or PET and the sheath is PE, or an eccentricity type sheath-core structure, or complex synthetic fiber of side-by-side structure. Moreover, it is also preferable to use the fiber by making it cloudy by mixing a filler comprising titanium oxide, calcium carbonate, etc. in a range of 0.5–1.0 m % as necessary.

The fiber length of the fiber used with the above spun lace non-woven fabric ranges 15–60 mm when it is natural cotton, and ranges 25–51 mm when it is rayon or acetate, and the fineness is to be selected from the range of 1.1–6.6 dtex. In this case, a preferred point is that use of fiber having a high specific surface area can increase a contact area with the inner wall of the labia, and is thereby able to decrease the risk of falling-off the interlabial product from the labia. For example, it is preferred to use rayon or acetate having a deformed (non-circular) cross section in which the fiber cross section is deformed like Y-type or C-type. It is also preferable that when the fiber is deformed in the cross section if compared to that with the cross section of perfect circularity, since the fiber is increased in the specific surface area as well as in the inter-fiber air gap, thereby, the surface side sheet is decreased in stiffness so that adhesion of the interlabial product to the inner wall of labia is improved, and that the risk of falling off the interlabial product from labia is reduced as well as the risk of menstrual blood leakage is.

As another preferred example of the surface side sheet, such spun lace nonwoven fabric can be used, wherein 15–5 m % synthetic resin, 50–10 m % natural cotton, and further 35–85 m % rayon or acetate are mixed in these proportion and adjusted to with a specific weight per unit area 20–50 g/m$^2$, and wherein the obtained spun lace is increased in width by about 10–80%, and further stretched in the longitudinal direction by about 10–80%. Since this spun lace nonwoven fabric has a high coarse-fineness gradient in a flat state, and is once relaxed in intertwining among fiber, this spun lace nonwoven fabric is the one wherein each fiber, especially, a synthetic resin having high single yarn stiffness is provided with a spring-back property, and has almost looped-form fiber projecting on the inner wall side of labia.

Since this looped-form fiber is able to relax frictional resistance in the shearing direction on the inner wall of labia and the surface of the interlabial product, the fiber is not only in less danger of hurting the inner wall of labia but is also able to reduce the flow velocity of menstrual blood flowing on the almost flat inner wall of labia toward underwear, and this helps the menstrual blood move to the absorbent body in the interlabial product.

The height and pitch of the loop-like form to be projected can be controlled by the method wherein the nonwoven fabric is varied in a widening rate and a drawing rate, or the nonwoven fabric is varied in intertwining force among the fiber according to the manufacturing method, or a composite synthetic resin of an eccentricity type sheath-core structure or a side-by-side structure is used and the percentage crimp of each single yarn of the fiber is adjusted by utilizing the differences among the thermal contraction ratio of the fiber.

As still another preferable example of the surface side sheet, a porous film made by perforation, heat-press, or the like of thermoplastic film, or a composite sheet of said film and nonwoven fabric can be mentioned. Among these, the nonwoven fabric part of said composite sheet provided with lots of nap-raised minute projections by means of water-jet treatment is more preferable. The surface resistance produced by said projections reduces the drift velocity of menstrual blood on the surface of the surface side sheet, and prevents the menstrual blood from flowing down and secures absorption of the menstrual blood. A height of the projections and a distance between them are preferred to be in a range of 0.1–4 mm.

Height and distance smaller than this range cause to decrease the gap for menstrual blood to flow into the interlabial product, and it becomes difficult to surely absorb the menstrual blood, while the height and distance exceeding this range may cause to get down the projections by body pressure or the like when the interlabial product is inserted, therefore, both cases are not preferable.

Moreover, the surface side sheet may entirely or partly be provided with holes, and a rate of the hole area is preferred to be in a range of 3–30%. A rate lower than this range has a less effect on menstrual blood moving to the side of the absorbent body, and a rate higher than this range reduces a ratio contact between the interlabial product and the inner wall of labia and so the interlabial product is in danger of falling from between labia, therefore, neither case is not preferable.

Among these materials, considering liquid movement from the inner surface of labia, chemical stimulus due to an activator, and adhesion to the inner wall of labia, such spun lace nonwoven fabric is preferred for the use, as rayon of 1.1–4.4 dtex fineness and 7–51 mm fiber length is laminated 40–80% to total specific weight per unit area on the body surface side; rayon of 1.1–4.4 dtex fineness and 7–51 mm fiber length which is 14–42% to total specific weight per unit area and PET which is 6–18% to the to total specific weight per unit area are mixed and laminated on the garment surface side; and the two layers are laminated so that the to total specific weight per unit area of both layers is 20–60 g/m$^2$; and then the fiber are intertwined by water jet intertwining and dried; and the thickness is adjusted within a range of 0.13–0.50 mm. In this case, since the bulkiness can easily be maintained by mixing PET in the rayon on the garment surface side even when the water-permeable sheet gets wet, the adhesion to the inner wall of labia can be maintained.

[Materials for Back Side Sheet]

As a material used for the back side sheet, a similar one to those for the surface side sheet can be used when a water-permeable material is used. In this case, it is preferable that the interlabial product is used together with a sanitary napkin (an interlabial product to be used with a sanitary napkin).

Further if non-water permeability material is used for said back side sheet, the menstrual blood, which is kept in the absorbent body, is prevented from a leak out of the interlabial product. Furthermore the pad can be comprised of water vapor permeability material, thereby in wearing the pad, the sweat and the discomfort can be lowered.

To apply materials of non-water permeability, non-water permeable film such as a thin filmed synthetic resin of PE, PP and the like, a gas-permeable film comprised of a synthetic resin filled with inorganic filler and processed with an extension treatment, a laminated film combined with of a paper nonwoven fabric and non-water permeable film, a nonwoven fabric of a spun bond or a spun lace which are treated with a water repellent with a gas-permeable resin film bonded on a rear surface thereof may be preferably used. Further for a method of providing ventilation on non-water permeability sheet, it is eligible to form a capillary having 10 to 30% of pore area ratios and a pore size of 0.1 to 0.6 mm toward the absorbent body.

More concrete example of applying non-water permeability materials, a film mainly of a low density polyethylene (LDPE) is eligible which is obtained from a range of a density 0.900 to 0.925 g/cm$^3$, with a specific weight per unit area 15 to 30 g/m$^2$, based on the total mass per unit area of the composition. The flexibility not to hurt a wear feeling is considered. More preferably, during the pad is attached between labia, non-water permeability sheets are contacted with each other, with the pad which is used together or with the under wear, to decrease a fear of dropping the interlabial pad from the labia due to the high friction, the film is treated an embossing process and the convex upheaval portion is disposed, thereby it may decrease a ratio contact by less frictional resistance.

[Absorbent Body]

Materials to be used for the absorbent body contained in the interlabial pad include pulp, chemical pulp, rayon, acetate, natural cotton, water-absorbent polymer, fibrous water-absorbent polymer, synthetic fiber or a mixture thereof. A mixture blended as predetermined is made into a sheet by technologies such as pressure bonding by embossing process, entanglement by needling that are well known in the art. The sheet may be adjusted by bulking, layering, folding, etc. as required.

Materials for the sheet may be used in a sheet or powdered. Their types of usage are not particularly limited.

It is preferable for the absorbent body, although any material can be used as long as it is capable of absorbing and holding liquid (body fluid), to be bulky, hard-to-be deformed, less chemically stimulant, and highly flexible to fit into the labia. Specifically, a nonwoven fabric sheet in which, 50 to 150 g/m$^2$ of pulp selected from the range of the fiber length of 1 to 10 mm is laminated on the garment face side and, on the body face side, 150 to 250 g/m$^2$ of a mixture obtained by mixing 60 to 90% of rayon with 1.1 to 4.4 dtex fineness and 20 to 51 mm fiber length with 40 to 10% of natural cotton by this mixing ratio is laminated, which then to be formed into a sheet by dotted emboss processing to have 2 to 10 mm bulkiness, and more preferable to have 3 to 5 mm bulkiness. Thereby, liquid can be easily transferred from the body face side to the garment face side resulting in the improvement of the absorbing and holding capacity. Furthermore, by providing a mesh spun lace nonwoven fabric of rayon with 1.1 to 4.4 dtex fineness and 25 to 51 mm fiber length by a specific weight per unit area of 15 to 40 g/m$^2$, the liquid transferred from the body face side can be diffused by the mesh spun lace to be induced to almost all over the region of the pulp layer. Therefore, more liquid can be effectively absorbed.

[Adhesive Portion]

In order to further reduce the danger that the interlabial product may fall off labia, it is preferable to form an adhesive portion by applying an adhesive agent on the surface of the surface side sheet for covering these. The interlabial product is reduced in the danger of falling by adhering the adhering portion in the neighborhood of the labia of a wearer.

As the arrangements of the adhesive portion, a plane form, a dotted form, a mesh form, a striped form, or the like can be employed. The position of the adhesive portion is not to be specifically limited as long as it is possible to fix the product to the body, however, the adhesive portion is preferred to be arranged in a striped form of about 1–5 mm in width in the longitudinal direction, considering the neighborhood of labia, especially, the existence of pubic hairs in front of labia.

"Adhesive portion" can be formed by applying an adhesive agent on the surface side sheet. As the adhesives which can be used in the present invention, a gel adhesive etc. comprising water-soluble polymer, crosslinking agent, plasticizer, or water content can be mentioned. To be more concrete, as examples of the water-soluble polymers, gelatin, polyacrylic sodium, polyvinyl alcohol, carboxyl-methyl-cellulose, etc. can be mentioned; as examples of the crosslinking agents, water-soluble metal salt such as calcium chloride, and magnesium sulfate; and as examples of the plasticizers, glycerine, wax, paraffin, etc. can be used.

In addition to the above, a pressure-sensitive hot melt adhesive can also be used as an adhesive for forming the adhesive portion. The pressure-sensitive hot melt adhesive comprises a synthetic rubber resin such as styrene-isoprene-styrene block copolymer (SIS), styrene-butadiene-styrene block copolymer (SBS), styrene-ethylene-butadiene-styrene block copolymer (SEBS), or styrene-ethylene-propylene-styrene block copolymer (SEPS), and can be obtained by melt-blending therein a tackifier such as turpentine resin and rosin resin, and a plasticizer such as wax.

Further, silicone resin adhesives can be used. As the silicone resin adhesive, a mixture composed by blending of crosslinking agents which essentially comprise silicone resin or fluorocarbon polymer and is metal salt of platinum, molybdenum, antimony, etc., and a polymerizer such as ester wax, glycerine, machine oil, etc.

Thus, there are many kinds of adhesives for forming the adhesive portion, however, considering the stability of application, a pressure sensitive hot melt adhesive is preferred for the use. As the pressure sensitive hot melt adhesive with high application stability, a melt-blended mixture of 15–25 m % SEBS, 15–35 m % plasticizer, and 40–70 m % tackifier can be mentioned. An oxidation inhibitor, a fluorescence inhibitor, etc. may be added to this pressure sensitive hot melt adhesive within a range of 0.1–1.0 m %.

[Structure of the Interlabial Pad Provided with Biodegradability, Water Dispersibility and Water Solubility]

Preferably the interlabial product according to the present invention is comprised of a material of biodegradability and/or a material of water dispersibility and/or a material of water-solubility. After using the product comprised of these materials, it can be disposed into a toilet to flush, thereby the destruction of the product can be easily and sanitarily achieved and the garbage in a toilet can be decreased.

In this Specification, "biodegradability" means that a substance is decomposed into gas such as carbon dioxide or methane, water, and biomass under anaerobic or aerobic condition according to the natural process under the existence of bacteria represented by actinomycetes and other microbes, and also means that the biodegradability (biodegradable rate and biodegradable degree) of the substance equals to a material naturally generated such as fallen leaves or a synthetic polymer generally recognized having the same biodegradability under the same environment. "Water dispersibility" means the same as water degradability, where there is no effect from the limited amount of water (menstrual blood) upon use, whereas in conditions of large amounts of water or under water flow, the fibers are easily dispersible into at least small pieces which cannot clog the toilet plumbing. "Water solubility" means the property of not being affected by limited amount of water (menstrual blood) upon use, but being soluble in large amounts of water or under a flow of water.

[Surface Side Sheet]

As a material for the surface side sheet for providing it with biodegradability, water dispersibility, and water solbility, spun lace non-woven fabric can be used, and it is also preferable to use wet spun lace non-woven fabric of which the fiber length is in a range of 1–15 mm. As the other materials, what is called biodegradable resin such as polylactic acid and poly-butylene succinate can also be used, for example, it is also preferred to use melt-blown non-woven fabric made from polylactic acid as a raw material and adjusted to with a specific weight per unit area 20–60 g/m$^2$, and spun bond non-woven fabric of which the specific weight per unit area is in a range of 15–30 g/m$^2$ and the fineness is adjusted to 1.1–3.3 dtex. As the other materials, a dissolved fiber from fiber composites by adjusting so-called tow in a range of 10–80 g/m$^2$ may be used. The tow may include acetate, rayon, synthetic resin by itself or a combination thereof.

[Absorbent Body]

Same materials having water permeability for the cover sheet can be used for materials of the absorbent body to apply biodegradability, water dispersibility and water solubility. Further it is possible to independently use the absorbent materials such as alginic acid soda, starch, carboxymethylcelluloce and the like, particle-typed or fiber-typed super absorbent polymer, or to use a form by mixing these materials with same materials for the cover sheet, In respect of the structure of the absorbent body; the wood pulp and the like are eligible, that is laminated to with a specific weight per unit area 150 to 500 g/m$^2$ to enclose into tissue and is adjusted the thickness from 2 to 10 mm by a press device. It is possible to improve the absorption capacity or keeping ability of the menstrual blood by mixing absorbent body such as starch and the like in a ratio from 5 to 30 g/m$^2$.

[Back Side Sheet]

As the materials for the back side sheet which can be provided with biodegradability, water dispersibility, and water solubility, and which is also water impermeable, laminated paper etc. can be mentioned, which laminates a film made from what is called biodegradable resin such as a polyvinyl alcohol (PVA) film, a film sheet provided with water-repelling treatment with silicone resin etc. on a part or the whole of one side or both sides of PVA film, a PVA film mixed with silicone resin, a starch film, polylactic acid or poly-butylene succinate, etc., and tissue etc. These materials may be mixed with inorganic pigments in a range of 0.1–5% to be colored as appropriate.

As a specific constitution of a water-impermeable back side sheet, for example, laminated paper can be mentioned, which is formed by laminating a film comprising polylactic acid, and 10–20 μm thick tissue with a specific weight per unit area in a range of 15–20 g/m$^2$ within a range of 5–40% lamination area ratio. It is preferable that such laminated paper is able to maintain water-impermeable property when the interlabial product gets wet, and does not charge a too heavy burden to a septic tank.

[Bonding Method]

Further for a bonding method of applying biodegradability, water dispersibility, water solubility, a bonding method such as adhesion by polyvinyl alcohol and the like having water solubility or water swelling, a heat sealing, or a bonding by a hydrogen bonding, and the like can be used individually or can be used in a combination of them adequately.

[Manufacturing Method]

The interlabial product constituted of such materials in accordance with the present invention can be manufactured by the following manufacturing method comprising:

a. a process for forming the shape of the absorbent body into a predetermined form, b. a process for laminating the surface side sheet wider than the absorbent body on the body surface side of the absorbent body, and laminating the back side sheet wider than the absorbent body on the garment side of the absorbent body, c. a process for bonding the surface side sheet and the back side sheet with each other on the periphery of the absorbent body, to form an absorbing layer, d. a process for folding the absorbing layer along the longitudinal center line in the lateral direction so that both side edge portions of the back side sheet are meet each other, e. a process for partly bonding the overlapping peripheral portions, and f. a process for forming the outer contour by cutting.

As to the process a, the absorbent body is cut into the prescribed form by being made to pass between a roll cutter provided with a cemented carbide edge and an anvil serving as a receiving roller.

Peripherals necessary for cutting the absorbent body into a shape are sucked to the side of the anvil roll provided with suction holes and are then supplied to a pipe for dust collection and collected.

Or, this may be such a process as forms the shape of the absorbent body by sucking and accumulating the pulverized particles such as pulps on meshes forming a prescribed shape and transcribing them on a conveyor belt with suction.

As to the process b, this may be provided with a process for applying an adhesive between the absorbent body and the surface side sheet, and the absorbent body and the back side sheet. For example, when a hot-melt type adhesive is applied, the hot melt melted by heating in a temperature range of 140–180 deg is press-fed into a supply hose by a gear pump and fed into a manifold for uniformalizing the flow rate distribution of the hot melt, and then a press-output rate is adjusted to 3–50 g/m$^2$ a specific weight per unit area and pressed out of a nozzle.

As to the process c, the absorbent layer is made to pass between an embossing roller on which a press-pattern is stamped and the anvil roller serving as a receiving roller, heating the absorbent layer at a temperature range of 70–160 deg, and pressing on it at a pressure rage of 1–3 MPa, to bond the peripheral portions. When the peripheral portions are bonded with a hot-melt type adhesive, or they are bonded by applying the hot-melt type adhesive using heat-sealing together, the adhesive is applied according to the method of the process b.

As to the process d, the absorbing layer obtained by the process c is folded in the lateral direction so that the side edges of the back side sheet are faced to each other by the sailor plates arranged on the right and left each so as to be gradually narrower in the travelling direction. In order to fold the absorbing layer almost along the longitudinal center line, an inducing line for folding it by applying pressure ranging 0.5–1 MPa onto a disk-like roller from the side of the back side sheet may be provided. Moreover, the inducing line for folding may be provided on the absorbent body. The inducing line is a metal mold roller with a 0.3–2 mm tip width, and is selected from a line form, a dashed line form, etc.

As to the process e, the folded absorbing layer is made to pass between the embossing roller stamped with the press-pattern thereon and the anvil roller serving as the receiving roller and thereby the peripheral portions are bonded by being pressurized at a range of 1–3 MPa at a temperature ranging 70–160 deg. There is no restriction for the embossing pattern, but a staggered pattern of a 2.5 mm width, a 0.5 mm² embossing area is intended at 0.5 mm intervals (in this embodiment).

As to the process f, the absorbent layer is made to pass between the roll cutter provided with the cemented carbide edge and the anvil roller, and the product is cut and formed into the outline in the folded state. The roll cutter is pressurized at a range of 0.5–2 MPa. The surplus disposal loss is sucked and supplied into the dust collection piping and collected.

[Individual Wrapping Body]

Figure 11:
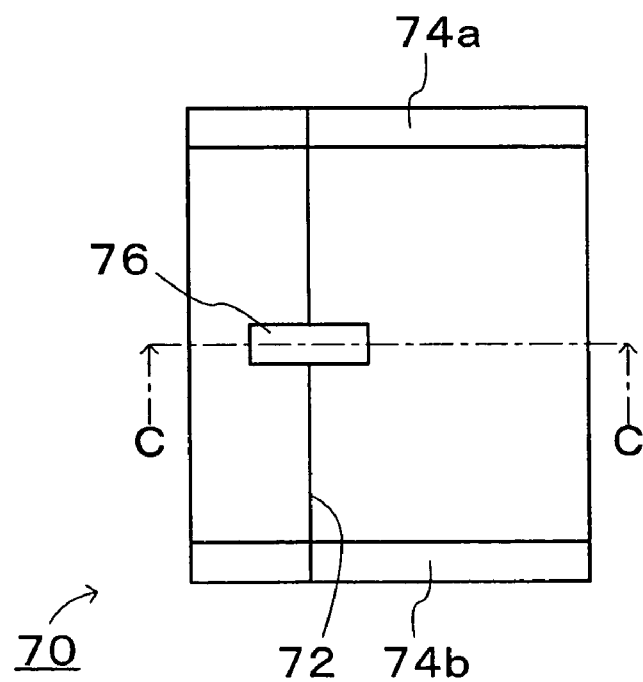
FIG. 11 is a top view of the interlabial wrapping body in accordance with one embodiment of the present invention.

FIG. 11 illustrates a top view of one embodiment of the individual wrapping body. The wrapping body 70 is formed lengthwise, and an unwrapped opening 72 is arranged so as to be opened in the lateral direction. The individual wrapping body 70 is formed by turning up both end portions of the wrapping sheet, and bonding the upper and lower end edge 74a, 74b of the wrapping sheet together to be strippable from each other. A tab tape 76 is attached on the overlapping part of the wrapping sheet in the center. The strippable bonding can be achieved by means of known techniques such as press-force by heat-embossing, and intertwining by male and female embossing.

Figure 12:
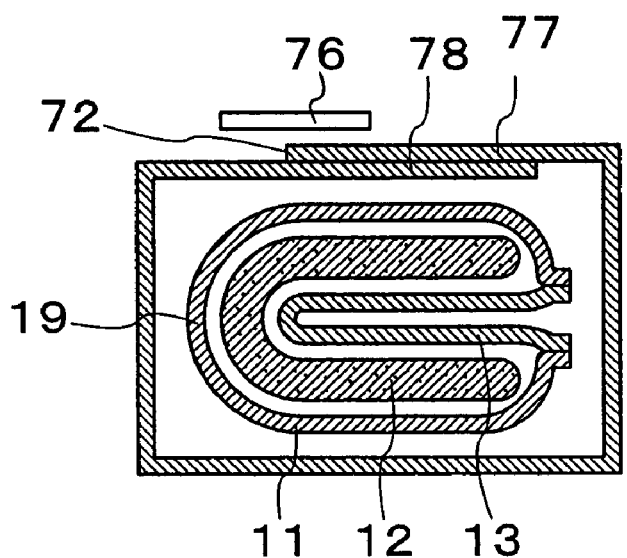
FIG. 12 is a cross-sectional view taken along the arrowed line C—C of FIG. 11.

FIG. 12 illustrates a cross-sectional view taken along the arrowed line C—C of FIG. 11. The wrapping sheet is folded with the end portion 78 thereof lower side and the end portion 77 thereof upper side, and the tab tape 76 is attached on the unwrapped portion 72. The interlabial product is enclosed in the folded state so that the back side sheet 13 is faced to each other almost along the longitudinal center line. A wearer picks up the tab tape 76, and carries out a work for taking out the interlabial product while breaking the strippable bonded portions 74a, 74b of the wrapping sheet.

Figure 13:
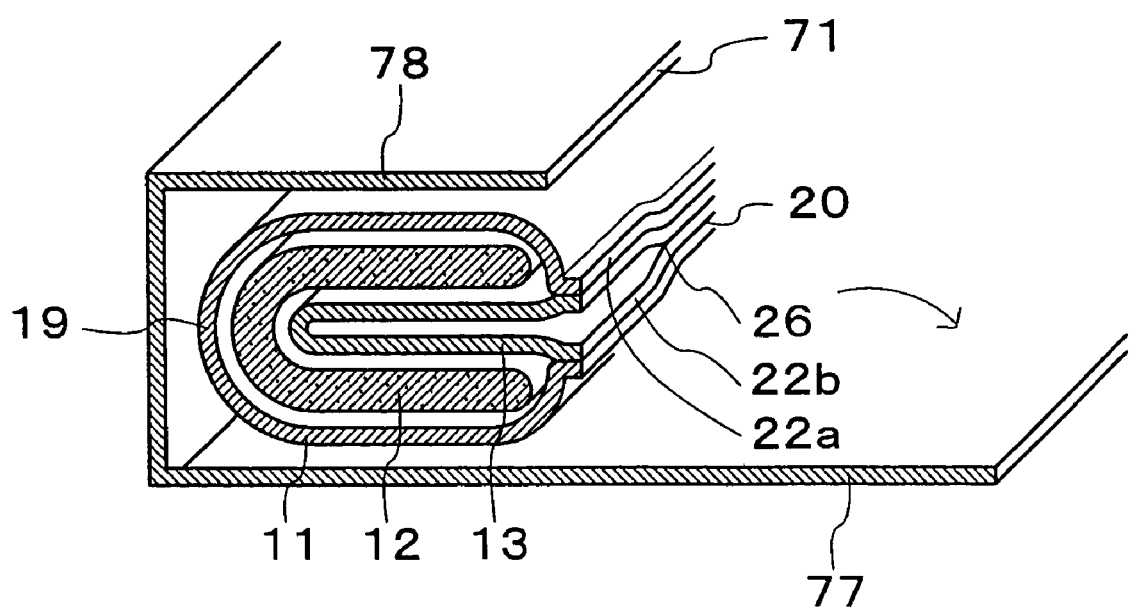
FIG. 13 is a perspective cross-sectional view showing the state in which one end portion 77 of the wrapping sheet is unwrapped.

FIG. 13 illustrates a perspective cross-sectional view of the state in which the wearer has opened the one end portion 77 of the wrapping sheet. The interlabial product is arranged so that the finger insertion opening 26 of the cylindrical portion 20 is positioned to face the unwrapped opening 71 of said individual wrapping body 70. The interlabial product is enclosed being folded so that the flap pieces 22a, 22b are opened when the interlabial product is unsealed. It becomes possible for the wearer to watch the cylindrical portion 20 of the enclosed interlabial product immediately when the product is unsealed, and to speedily secure the interlabial product by a finger.

In that case, the interlabial product is still enclosed in the other end portion 78 of the interlabial product and can be maintained via the wrapping sheet, so the surface side sheet 11 of the interlabial product does not come into contact with the finger, therefore, the interlabial product can be handled sanitarily also when it is taken out.

Moreover, since the wearer is induced into the state in which she holds the end portion 78 of the individual wrapping body enclosing the interlabial product by one hand at the time of unsealing it, such a trouble as the interlabial product may fall off the wrapping body can be prevented. The wearer picks up the tab tape by the other hand to open the end portion 77.

It is preferable that the unwapped opening 71 of the individual wrapping body is faced to the opposite side of the folded part 19 of the interlabial product. If the unwrapped opening 71 is faced to the same side of the folded part, the wearer observes the folded part of the interlabial product at the time of unsealing it, she has to turn the interlabial product enclosed in the wrapping body to find out the finger insertion portion formed on the rear surface side of the interlabial product, therefore, this makes the insertion operation complex and lacks in smooth insertion operation.

The wrapping material used for the wrapping sheet is chosen from a single use or lamination of tissue, non-woven fabric, film, etc., and is not to be restricted. To be specific, a film essentially comprising low-density polyethylene (LDPE) adjusted to a specific weight per unit area ranging 15–30 g/m² is used in general. Such a constitution is more preferable, as menstrual blood adhering to labia does not come into contact with the finger inserted in the sack at the time of insertion, lamination of non-woven fabric and a film can be used for the purpose. To be more concrete, a complex obtained by laminating a film essentially comprising LDPE adjusted to a specific weight per unit area ranging 5–20 g/m² on one side of complex non-woven fabric composed of spun bond, melt-blown and spun bond of 6–10 gsm, 5–20 gsm and 6–10 gsm by weight, respectively, can be used.

Moreover, when water washability is considered, the wrapping materials can be obtained from non-woven fabric or a film of biodegradable polylactic acid, poly-butylene succinate, polylactic acid, poly-isocyanate, starch, etc.; water-soluble materials can be obtained from a film essentially comprising of poly-vinyl alcohol; and toilet paper can also be used. To be concrete, lamination of a film of poly-isocyanate adjusted to a specific weight per unit area ranging 5–10 g/m² and water-soluble paper to be adjusted to a specific weight per unit area ranging 15–30 g/m² can be mentioned.

Since it becomes possible to re-enclose the interlabial product in the individual wrapping body after use by composing both of the individual wrapping body and interlabial product of water-soluble materials, the individual wrapping body and the interlabial product can be disposed of in a flushing toilet at the same time, and this facilitates disposal work.

[Method for Manufacturing Individual Wrapping Body]

The individual wrapping body for enclosing the interlabial product constituted as the above can be manufactured by the following manufacturing method provided with the following processes, that is;

a) a process for arranging the wrapping sheet at least on one side of either the upper surface or the lower surface to the transport direction of the interlabial product,
   b) a process for enclosing the interlabial product in the wrapping sheet by folding the end portion 78 of the wrapping sheet from the folding part 19 side of the interlabial product toward the peripheral bonding portion side of the interlabial product, then folding up one end portion 77 of the wrapping sheet from the peripheral bonding portion of the interlabial product toward the folding part 19 of the interlabial product, and overlapping the wrapping sheet with each other,
   c) a process for bonding the upper and lower end edges 74a, 74b of the wrapping sheet together, and
   d) a process for cutting the wrapping sheet into the prescribed dimensions.

In the process a), the wrapping sheet wider than the interlabial product is overlaid on the interlabial product.

In the process b), the interlabial product is enclosed in the wrapping sheet by folding one side 78 of the wrapping sheet from the folding part 19 side of the interlabial product toward the peripheral bonding portion side of the interlabial product, then folding up one side of the wrapping sheet from the peripheral bonding portion of the interlabial product toward the folding part 19 of the interlabial product, and overlapping the wrapping sheet with each other.

This method is to prevent such a mis-operation as a wearer has to open the wrapping sheet from the folded part of the interlabial product, by folding the wrapping sheet from the folded part 19 side of the interlabial product. Further, the folding width has such a dimension as is sufficiently able to cover the widthwise dimension of the interlabial product. Thus, it is possible to prevent a wearer's finger from touching the surface side sheet when she takes the interlabial product out of the wrapping body.

The wrapping sheet is folded by being guided from the folding part side of the interlabial product by the sailor plates arranged on the right and left each so as to be gradually narrower in the travelling direction, and is folded one by one to enclose the interlabial product.

In the process c), the wrapping sheet enclosing the interlabial product therein is made to pass between the embossing roller stamped with the press-pattern thereon and the anvil roller serving as the receiving roller, and the upper and lower end edges 74a, 74b of the wrapping sheet are bonded together by being pressurized at a range of 1–2 MPa at a temperature of 60–130 deg. Although the embossing pattern is not to be restricted, it may be provided with a 3–10 mm bonding length, and a lattice pattern with a 0.5 mm$^2$ embossing area and a 1.0 mm pitch may be used.

This process may be provided with a step for affixing a tab tape to stride over the overlapping part of the wrapping sheet. Or, the overlapping part may be coated with an adhesive for bonding the part. Such an arrangement makes it possible for a wearer to visually check the position of the unsealing part. Moreover, the arrangement prevents the entry of dust and dirt during storage and is sanitary.

In the process d), the wrapping sheet is made to pass between the roll cutter provided with a cemented carbide edge and the anvil roller, and the individual wrapping body is formed by cutting off the upper later sheet. The roll cutter is pressurized at 0.5–2 MPa. The surplus parts to be disposed of are sucked and supplied into the dust collection piping for collection. Both of the front and back sides of the individual wrapping body may be cut into curved surfaces.

[Another Embodiment of Individual Wrapping Body]

Another embodiment according to the present invention is described here.

Figure 14:
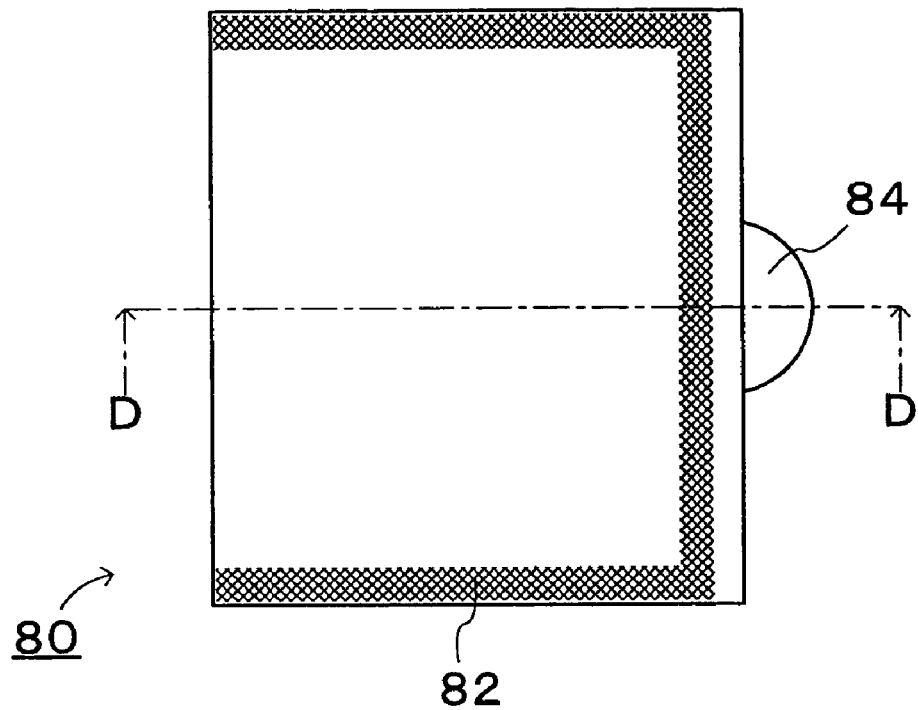
FIG. 14 is a schematic plan of the individual wrapping body in accordance with another embodiment of the present invention.
Figure 15:
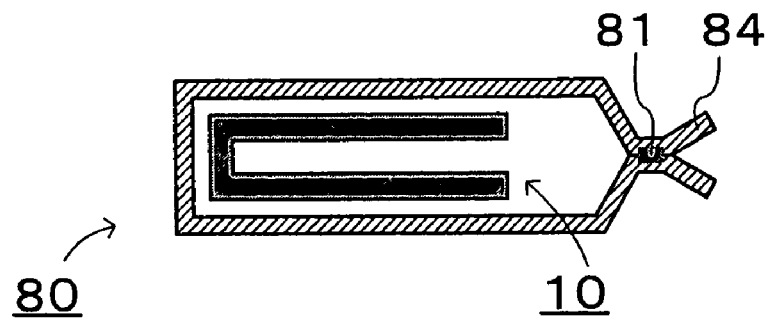
FIG. 15 is a schematic cross-sectional view taken along the arrowed line D—D of FIG. 14.

FIG. 14 is a top view outline of the individual wrapping body 80 in accordance with another embodiment of the present invention. FIG. 15 is a cross-sectional schematic taken along the arrowed line D—D of FIG. 14. In the embodiment in FIG. 14, the three sides 82 of the individual wrapping body are bonded to be strippable, to enclose the interlabial product inside. The tab 84 is a guide for the unsealing part. In FIG. 15, the interlabial product is folded in two in the lateral direction along the longitudinal center line. The figure illustrates the finger insertion opening of the interlabial product arranged on the side of the unsealing part 81 of the individual wrapping body.

As shown in FIG. 14, the interlabial product may be enclosed by folding a single wrapping sheet in half. Or, the interlabial product may be enclosed by superposing two wrapping sheets of the same shape on each other and bonding their four sides together so as to be strippable.

As shown in FIG. 15, the interlabial product is placed so that the finger insertion opening of the cylindrical portion of the interlabial product is positioned to face the unsealing hole 81 of said individual wrapping body 80.

Such a structure makes it possible for a wearer to visually check the finger insertion portion, namely, the cylindrical portion at the same time when she unseals the individual wrapping body.

Here, the tab is formed in a shape of a picking tab 84 on the individual wrapping body so that a wearer can visually check the position of the unsealing part, however, the tab shape is not to be restricted to this embodiment.

Figure 16:
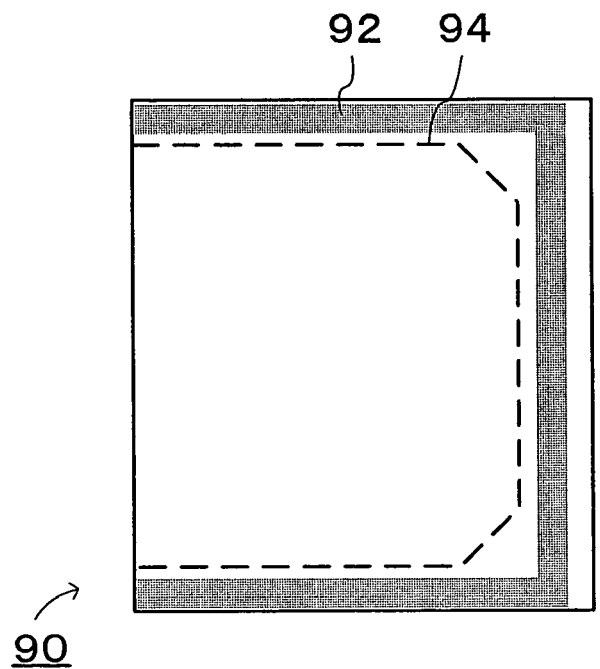
FIG. 16 is a schematic plan view of the individual wrapping body in accordance with another embodiment of the present invention.

FIG. 16 is a plane schematic of the individual wrapping body 90 in accordance with another embodiment of the present invention.

According to the embodiment shown in FIG. 16, in addition to the heat sealing 92, the unsealing part may be opened by breaking the perforations 94 arranged inside of the heat sealing 92.

The individual wrapping body is so structured that the wearer can visually check the finger insertion portion of the interlabial product through the broken opening of the perforations, and the edge portions of the three sides are bonded by heat sealing, and the perforations are provided inside of the edges.

As to the perforations, the tear part length is within a range of 0.5–5 mm, and the width is not wider than 3 mm considering the prevention of the entry of dust and dirt.

The position of the dashed line is preferred to start from one lengthwise side edge end of the individual wrapping sheet, and it does not matter whether the line is connected up to the other edge end or it is arranged from one edge end up to about the middle point. The breaking strength is within a range of 0.2-3.0N/25 mm in the lateral direction, and more preferably, 0.3–1.5N/25 mm (the breaking strength of the perforations, speed; 100 mm/min). In this case, the perforations make an unwrapped opening, therefore, the heat-sealing part 92 is preferred to be increased in the bonding strength so as not to be strippable, to avoid misunderstanding the operation.

Figure 17:
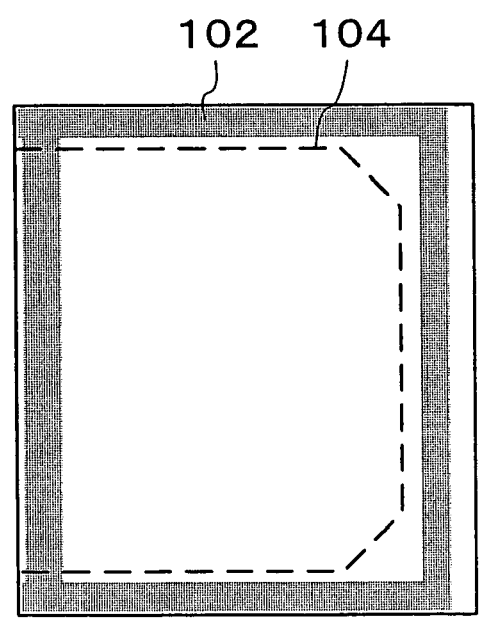
FIG. 17 is a schematic plan view of the individual wrapping body in accordance with another embodiment of the present invention.

FIG. 17 is a plane schematic showing an embodiment in which the interlabial product is held between two wrapping sheets and the four sides are bonded by heat sealing 102, and then the three sides are provided with the perforations 104.

With such an arrangement in both FIG. 16 and FIG. 17, a wearer can visually check the finger insertion portion as soon as she breaks the perforations. Moreover, since the interlabial product is grasped by the wearer's hand via the wrapping sheet, the insertion operation is sanitarily performed without contact between the surface side sheet of the interlabial sheet and the finger.

In both embodiments shown in FIG. 16 and FIG. 17, the individual wrapping body may be provided with a print (for example, an arrow head), different cut forms in the front and rear in the neighborhood of the beginning of the perforations (for example, the edge end is cut round), or the individual wrapping body made asymmetric in the longitudinal direction, etc., so as to visually suggest the wearer of the perforations.

When the individual wrapping body is made asymmetric in the longitudinal direction, by forming the individual wrapping body so that it gradually becomes wider toward one side end portion, making it face in the widening direction, making the finger insertion opening of the finger insertion portion face in the narrowing direction, and positioning the finger insertion portion to face in the widening direction, the wearer will naturally grasp it by hand on the narrower part, the finger insertion is directed toward the wearer at the same time as the wrapping body is opened.

INDUSTRIAL APPLICABILITY

Since the interlabial product of the present invention is provided with a cylindrical portion formed thereon in which a finger can be inserted, the finger can be secured until the interlabial product is taken out and inserted in labia, and the longitudinal direction of the interlabial product is naturally guided to the direction of the labia, and a wearer can insert the interlabial product while confirming the insertion point by securing the product with the ball of the finger faced to the side of the back side sheet.

What is claimed is:

1. An interlabial pad comprising:
   a water-permeable surface side sheet;
   a back side sheet;
   an absorbent body for absorbing body fluid disposed between the surface side sheet and the back side sheet; and
   a portion for forming a longitudinally elongated open space for inserting a finger therein,
   wherein said open space is formed inside the interlabial pad to extend from one end to another end of the interlabial pad along the longitudinal direction by attaching longitudinally opposing peripheral edges of the back side sheet in the longitudinal direction from approximately the middle of the peripheral edges towards one end of the peripheral edges, said open space becomes smaller toward the end of the peripheral edges, and a part of the peripheral edges of the back side sheet away from the end of the peripheral edges is opened to form a finger insertion opening, and said interlabial pad has a size adapted to be disposed between the labia of a wearer.

2. The interlabial pad according to claim 1, further comprising:
   a flap portion provided longitudinally adjacent to said portion,
   wherein said flap portion is formed by a pair of flap pieces not bonded to each other to define a finger insertion opening.

3. A method for manufacturing an individual wrapping body comprising:
   a process for folding the interlabial pad according to claim 2 in two parts in a lateral direction along a longitudinal center line, and
   a process for enclosing said interlabial pad in the wrapping sheet.

4. The interlabial pad according to claim 1, wherein said portion is extended up to an end portion of the interlabial product along the finger insertion direction, and that said portion covers a wearer's finger inserted in said portion.

5. The interlabial pad according to claim 1, wherein said portion is extensible or elastic at least in a lateral direction.

6. The interlabial pad according to claim 1, wherein a tacking agent is applied on an inner surface of said portion for a fingertip of the finger.

7. The interlabial pad according to claim 1, wherein said absorbent body is enclosed between said surface side sheet and said back side sheet, and
   wherein said back side sheet is disposed inside of said portion.

8. The interlabial pad according to claim 1, wherein said absorbent body and said back side sheet are enclosed in said surface side sheet, and
   wherein said surface side sheet is disposed inside and outside of said body.

9. The interlabial pad according to claim 1, wherein said interlabial product is a product for incontinence.

10. The interlabial pad according to claim 1, wherein said interlabial product is a product for absorbing vaginal discharge.

11. An individual wrapping body comprising the interlabial pad recited in claim 1, and a wrapping sheet for entirely covering and enclosing said interlabial pad.

12. The individual wrapping body according to claim 11, wherein said interlabial pad is folded up and enclosed so that the flap pieces open when the individual wrapping body is unwrapped.

13. The individual wrapping body according to claim 11, wherein said individual wrapping opening formed on a surface of the wrapping sheet, and the interlabial pad is disposed so that the finger insertion opening of said portion is positioned to face the unwrapping opening of said individual wrapping body.

14. A method for manufacturing an individual wrapping body comprising:
   a process for folding the interlabial pad according to claim 1 in two parts in a lateral direction along a longitudinal center line, and
   a process for enclosing said interlabial pad in the wrapping sheet.

15. An interlabial pad comprising:
   a water-permeable surface side sheet;
   a back side sheet;
   an absorbent body disposed between the surface side sheet and the back side sheet; and
   a portion for forming a longitudinally elongated open space for inserting a finger therein, said portion formed by attaching opposing peripheral edges of the back side sheet in the longitudinal direction from approximately the middle of the peripheral edges towards amend of the interlabial pad, said portion having an finger insertion opening at an end away from said end of the interlabial pad, and said open space becoming smaller towards the end of the interlabial pad away from the finger insertion opening,
   wherein said interlabial pad has a size adapted to be disposed between the labia of a wearer.

* * * * *